United States Patent [19]

Desbordes et al.

[11] Patent Number: 5,100,460
[45] Date of Patent: Mar. 31, 1992

[54] HERBICIDAL COMPOUNDS AND COMPOSITIONS CONTAINING THEM

[75] Inventors: Philippe Desbordes; Michel Euvrard, both of Lyons, France

[73] Assignee: Rhone-Poulenc Agrochimie, Lyons, France

[21] Appl. No.: 379,418

[22] Filed: Jul. 13, 1989

[30] Foreign Application Priority Data

Jul. 13, 1988 [FR] France ................. 88 09769

[51] Int. Cl.$^5$ ............... A01N 37/18; A01N 37/34; A01N 31/00; A01N 31/04
[52] U.S. Cl. ............... 71/94; 546/310; 546/311; 546/312; 546/314; 546/315; 546/316; 546/323; 546/328; 546/330; 546/334; 546/337; 546/339; 546/256; 546/261; 546/264; 546/265; 546/266; 546/267; 546/283; 546/284; 546/286; 546/287; 546/288; 546/289; 546/291; 546/296; 546/297; 546/298; 546/299; 546/300; 546/301; 546/302; 546/304; 546/307; 546/308; 546/309; 549/90; 549/551; 549/553; 549/554; 549/561; 549/562; 558/411; 558/413; 558/414; 558/418; 558/420; 558/423; 558/424; 558/425; 71/88; 71/98; 71/103; 560/227; 560/228; 560/129; 560/229; 560/230; 564/152; 564/153; 564/154; 564/162; 564/307; 564/430; 564/440; 568/27; 568/28; 568/29; 568/30; 568/31; 568/32; 568/33; 568/34; 568/35; 568/36; 568/37; 568/38; 568/39; 568/41; 568/42; 568/43; 568/44; 568/45; 568/49; 568/50; 568/51; 568/52; 568/54; 568/56; 568/57; 568/58

[58] Field of Search ............ 71/94, 98, 88, 103; 558/411, 413, 414, 418, 420, 423, 424, 425; 560/227, 228, 129, 229, 230; 564/152, 153, 154, 162, 307, 430, 440; 568/27, 28, 29, 30, 31, 32, 33, 34, 35, 36, 37, 38, 39, 41, 42, 43, 44, 45, 49, 50, 51, 52, 54, 56, 57, 58; 549/90, 551, 553, 554, 561, 562

[56] References Cited

U.S. PATENT DOCUMENTS 4,677,128  6/1987  Place et al. .................. 71/90

FOREIGN PATENT DOCUMENTS 0326170  2/1984  European Pat. Off. .
157712   10/1985 European Pat. Off. .
0281110  7/1988  European Pat. Off. .
63-244796 10/1988 Japan .

OTHER PUBLICATIONS

Fox et al., Chem. Abstracts, vol. 98, No. 15; 125115w (1983).
Bravo et al. Chem. Abstracts, vol. 113, No. 3; 2329k (1990).
Desbordes et al. Chem. Abstracts, vol. 112, No. 23; 212484s (1990).

Primary Examiner—Johann Richter

Attorney, Agent, or Firm—Scully, Scott, Murphy & Presser

[57] ABSTRACT

Herbicides of formula:

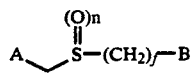

I in which:
n=0, 1, 2
f=0, 1
A is chosen from the groups

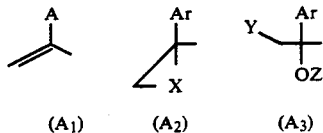

(A₁)    (A₂)    (A₃)

in which:
Ar is chosen from the groups

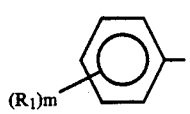

Ar-1

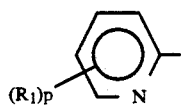

Ar-2

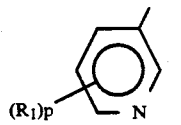

Ar-3

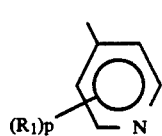

Ar-4

B is chosen from optionally substituted $C_1$-$C_{10}$ alkyl and $C_3$-$C_{10}$ cycloalkyl groups or from the groups

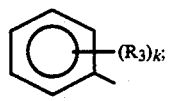

B₁

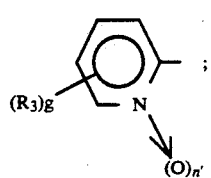

B₂

(Abstract continued on next page.)

-continued
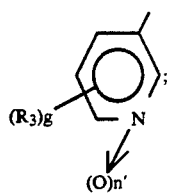
B₃
-continued
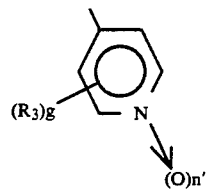
B₄
14 Claims, No Drawings

HERBICIDAL COMPOUNDS AND COMPOSITIONS CONTAINING THEM

The invention relates to new compounds, to their use as herbicides, especially in the form of a herbicidal composition, and to a process for controlling weeds with the aid of these compounds or of these compositions.

An objective of the present invention is therefore to propose compounds which can be used in pre- or post-emergence as herbicides.

Another objective of the present invention is to propose compounds which can be used in pre- or post-emergence as antigraminaceous herbicides.

Another objective of the present invention is to propose compounds which can be used in pre- or post-emergence as selective herbicides for maize and for many dicotyledon crops (especially soya, rape, sunflower, cotton) and other monocotyledon crops (wheat, rice).

GENERAL DEFINITION OF THE INVENTION

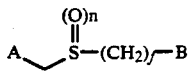

in which:
n = 0, 1, 2
f = 0, 1
A is chosen from the groups

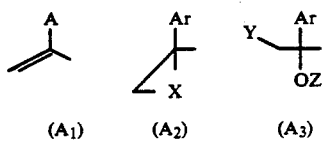

in which:
Ar is chosen from the groups

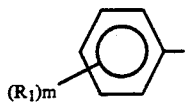   Ar-1

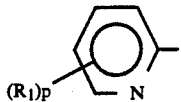   Ar-2

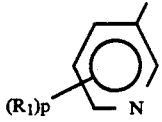   Ar-3

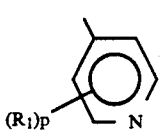   Ar-4

X being an oxygen or sulphur atom, $R_1$ being a halogen atom (especially Cl or Br or F) or a $C_1$-$C_4$, $C_1$-$C_4$ alkoxy, $C_1$-$C_4$ haloalkyl, $C_1$-$C_4$ haloalkoxy, nitro, cyano, $C_6$-$C_{10}$ aryl (especially phenyl or naphthyl), $C_7$-$C_{11}$ aralkyl (especially benzyl), $C_6$-$C_{10}$ aryloxy (especially phenoxy or naphthoxy) optionally substituted by 1 or 2 halogen atoms, or $C_7$-$C_{11}$ aralkyloxy (especially benzyloxy) group, optionally substituted by 1 or 2 halogen atoms, m = 0, 1, 2, 3, 4, 5
p = 0, 1, 2, 3, 4 the various radicals $R_1$ being identical or different when m or p is greater than or equal to 2.

Y is a chlorine or bromine or iodine atom or an $OSO_2R_2$ group, $R_2$ being a $C_1$-$C_6$ alkyl, $C_6$-$C_{10}$ aryl or $C_7$-$C_{11}$ aralkyl group, the said groups being optionally substituted by 1 to 3 halogens or $C_1$-$C_4$ alkyl, $C_1$-$C_4$ alkoxy, $C_1$-$C_4$ haloalkyl, $C_1$-$C_4$ haloalkoxy or nitro groups, Z being a hydrogen atom or a (C=O)$R_{11}$ group,
$R_{11}$ is hydrogen, $C_1$-$C_4$ alkyl, $C_1$-$C_4$ haloalkyl, B is chosen from the $C_1$-$C_{10}$ alkyl and $C_3$-$C_{10}$ cycloalkyl groups, these groups being optionally substituted by 1 to 6 halogen atoms or is chosen from the groups

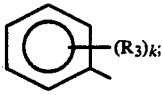   $B_1$

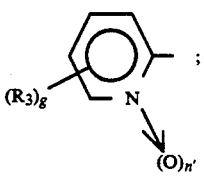   $B_2$

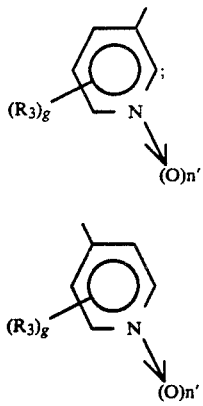

$R_3$ having one of the meanings shown for $R_1$ or $NR_4R_5$, $S(O)_hR_6$ or $(C=O)R_7$, $R_4$ and $R_5$, which are identical or different, are hydrogen, $C_1$-$C_4$ alkyl or $C_6$-$C_{10}$ aryl, $R_6$ is $C_1$-$C_4$ alkyl, $R_7$ is $C_1$-$C_4$ alkyl, $C_1$-$C_4$ alkoxy, $C_1$-$C_4$ haloalkoxy or $NR_9R_{10}$, p0 $R_9$ and $R_{10}$, which are identical or different, are hydrogen or $C_1$-$C_4$ alkyl, $K = 0, 1, 2, 3, 4, 5,$
$g = 0, 1, 2, 3, 4,$
$h = 0, 1, 2,$
$n' = 0, 1.$

PREFERRED VARIANTS

According to the preferred methods of preparation, the following variants will be chosen, taken in combination or otherwise:

n = 2
X = 0
Z = H
m smaller than or equal to 2
p smaller than or equal to 2
k smaller than or equal to 2
g smaller than or equal to 1
$R_1$ is halogen, nitro, trifluoromethyl, methoxy or methyl.

The compounds of formula I and the compounds which may optionally be employed as intermediates in the preparative processes and which will be defined when these processes are described can exist in one or more isomeric forms depending on the number of asymmetric centers in the molecule. The invention therefore also relates to all the optical isomers and their racemic mixtures and the corresponding diastereoisomers. The separation of the diastereoisomers and/or of the optical isomers can be carried out according to methods which are known per se.

PREPARATIVE PROCESSES

Method A

The compounds of formula (I) for which n = 2, and A is (A1), the other substituents having the same definition as that shown in the general definition of the invention, may be obtained by bringing a compound of formula:

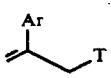   II in which Ar, $R_1$ and m or p have the same meaning as in the general definition of the invention and T is a chlorine or bromine atom, into contact with a compound of formula:

$$MSO_2(CH_2)_f\text{—}B \qquad III$$

f and B having the same definition as that shown in the definition of the invention, M being an alkali or alkaline-earth metal atom (especially Li, K, Na).

The reaction is generally carried out in a dipolar aprotic solvent, especially dimethylformamide or N-methylpyrrolidone, at a temperature of between 25° C. and 150° C. (preferably 60° C. to 120° C.) and in a molar ratio II:III of between 1 and 10 (preferably 1 and 2).

This reaction is known particularly from J. March, "Advanced Organic Chemistry", McGraw-Hill publ. (1985), p. 363.

The compounds of formula (II) where T is chlorine and Ar is Ar-1 (phenyl nucleus) are prepared by chlorination of a 2-phenyl-1-propene compound of formula:

   IV in which

Ar is Ar-1 (phenyl nucleus), $R_1$ and m having the same meaning as in the definition of the general formula, by means of the reactant Ca(OCl)$_2$/CO$_2$.

This reaction is described by S. G. Hegde and J. Wolinsky, Tetrahedron Letters (1981), 22, 5019.

The compounds of formula (II) where T is chlorine, Ar having the same definition as that shown in the general definition of the invention, can also be prepared by chlorination of the compounds of the above-mentioned formula (IV) by means of N-chlorosuccinimide in the presence of bisaryl diselenide according to the process of K. B. Sharpless and T. Hori, J. Org. Chem. (1979), 44, 4204.

The compounds of formula (II) where T is chlorine or bromine, Ar having the same definition as that shown in the general definition of the invention, can also be prepared by thermal or photochemical radical halogenation of the compound of formula (IV), using an N-halosuccinimide in an aprotic solvent such as carbon tetrachloride, or in the absence of solvent with or without a free-radical initiator at a temperature of 20° C. to 170° C. (preferably 80° C. to 100° C.) according to S. F. Reed, J. Org. Chem. (1965), 30, 3258. They can also be prepared by halogenation of the compounds of formula (II) where T is OH, Ar having the same definition as that shown in the general definition of the invention, with a halogenating agent such as SOCl$_2$, POCl$_3$ or PBr$_3$, ibid. J. March p. 382-384 or with a LiCl/CH$_3$SO$_2$Cl/collidine mixture according to E. W. Collington and A. I. Meyers, J. Org. Chem. (1971), 36, 3044.

The compounds of formula (II) where T is OH, Ar having the same definition as that shown in the general definition of the invention, can be prepared by allylic oxidation of the compound of formula (IV) by means of selenium oxide, catalytic or otherwise, in the presence of an oxidizing agent such as tert-butyl hydroperoxide in an inert solvent such as halogenated solvents (preferably CH$_2$Cl$_2$) or tert-butanol, in the presence of an inorganic or organic acid, according to M. A. Umbreit and K. B. Sharpless, J. Amer. Chem. Soc. (1977), 99, 5526.

The compounds of formula IV can be obtained by dehydration of a 2-aryl-2-propanol compound of formula:

   V in which Ar, $R_1$ and m or p have the same meaning as in the general definition of the invention, by means of dehydrating agents such as $P_2O_5$, $KHSO_4$ and $POCl_3$./pyridine, ibid , J. March, p. 901-903.

The compounds of formula (V) can be prepared by bringing the acetophenone or acetylpyridine or acid derivative of formula:

   VI in which Ar, $R_1$ and m or p have the same meaning as in the general definition of the invention and W is methyl, alkoxy (corresponding benzoic ester) or chlorine, into contact with one or two equivalents of methylmagnesium halide, according to J. March, ibid. p. 816-822.

The compounds of formula (VI) are obtained in a manner which is known per se.

The compounds of formula (III) can be prepared by reduction of the corresponding sulphonyl halides (generally chloride) using zinc, sodium or potassium iodide or sodium sulphite, according to J. March, ibid. p. 445-446. The sulphonyl halides can be prepared according to J. March, ibid. p. 1172.

The compounds of formula (III) can also be prepared by reaction of an organometallic (usually lithium) derivative of formula:

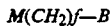   IIIA f and B having the same meaning as that shown in the definition of the invention, M being especially lithium, with sulphur dioxide $SO_2$, at a temperature of between $-78°$ C. and 20° C. (preferably $-78°$ C. to $-40°$ C.) in the absence or in the presence of an aprotic solvent such as ethyl ether or tetrahydrofuran, according to H. W. Pinnick and M. A. Reynolds, J. Org. Chem. (1979), 44, 160, and J. March, ibid, p. 550.

The compounds of formula (IIIA) are obtained in a manner which is known per se.

The compounds of formula (III) in which B is $B_1$, $B_2$, $B_3$ or $B_4$ and f=0 can also be prepared by reaction of the corresponding aryl diazonium salt with sulphur dioxide $SO_2$ in the presence of copper, according to W. E. Truce and A. H. Murphy, Chem. Rev. (1951), 48, 69 and cited references.

Method B

The compounds of formula (I) in which A is ($A_1$) and n=0, 1 or 2 can be prepared by reaction of the alkali metal salt of an aryl or alkyl thiolate of formula:

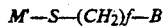   VII in which M' is an alkali or alkaline-earth metal atom, especially Na or K, f and B having the same definition as that shown in the definition of the invention, with a compound of formula (II) where T is halogen, described previously, in a protic or aprotic inert solvent such as ketones, alcohols, tetrahydrofuran or acetonitrile, at a temperature of 0° C. to 80° C. (generally 25° C. to 60° C.) in a molar ratio II:VII which is generally between 1 and 10 (preferably 1 and 2).

The sulphide thus obtained (n=0) can be oxidized to a sulphoxide (n=1) using one equivalent of oxidizing agent at a temperature of $-70°$ C. to 5° C. (generally 0° C.) or can be oxidized to a sulphone (n=2) using two or more equivalents of oxidizing agent at a temperature of 0° C. to 60° C. (generally 10° C. to 30° C.) using numerous oxidizing agents such as $KMnO_4$, $H_2O_2$, $CH_3CO_3H$, perbenzoic acids, $KHSO_5$, and others, according to very many known methods (ibid. J. March p. 1089-1090).

In the case where B is $B_2$, $B_3$ or $B_4$ and n'=0, an oxidizing agent which is specific for sulphur, such as tetrabutylammonium hydrogen persulphate, will be chosen, according to B. M. Trost and R. Braslau, J. Org. Chem. (1988), 53, 532.

Method C

In the case where n=2 and A is ($A_1$), another process for the preparation of the compounds of formula (I) consists in reacting the compound of formula (IV), described previously, with the compound of formula (III), described previously, in an aprotic inert solvent such as acetone, ethyl acetate or acetonitrile in the presence of a protic solvent (preferably $H_2O$) with one equivalent of iodine at ambient temperature according to L. M. Harwood and M. Julia, Tetrahedron (1980), 36, 483 and T. Kobayashi et al., Chem. Letters (1987), 1209.

Method D

The compounds of formula (I) in which A is ($A_1$), n=1 or 2, the other substituents having the same definition as that shown in the general definition of the invention can be obtained by bringing the anion of a dialkyl or aryl aryl- or alkylsulphonomethylphosphonate of formula:

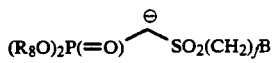   VIII or the anion of a dialkyl or aryl aryl- or alkylsulphinomethylphosphonate of formula:

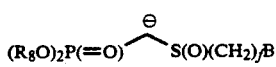   IX in which formulae $R_8$ is a $C_1$-$C_4$ alkyl or $C_6$-$C_{10}$ aryl group, f and B having the same definition as that shown in the general definition of the invention, into contact with an acetylpyridine or acetophenone of formula (VI) in which W is methyl and Ar, $R_1$ and m or p have the same meaning as in the general definition of the invention.

The reaction is carried out in a molar ratio VI:VIII or IX which is generally between 1 and 5 (preferably 1 and 2), in an aprotic solvent such as tetrahydrofuran in the presence or absence of a dipolar aprotic solvent such as hexamethylphosphotriamide, at a temperature of $-78°$ C. to 80° C. (preferably $-78°$ C. to 40° C.) to give the compounds of formula X:

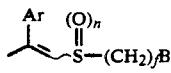   X in which Ar, $R_1$, m, p, f and B have the same meaning as in the general definition of the invention and n=1 or 2, according to H. Fillion et al., J. Heterocyclic Chem. (1978), 15, 753.

The anions of formulae (VIII) and (IX) are prepared by reaction of a base such as NaH or BuLi with the corresponding compounds.

The compounds of formula (I) in which A is (A) and n=1 or 2 are obtained by isomerization of the compounds of formula (X) in a basic medium using 1 to 5 (preferably 2) equivalents of base such as potassium tert-butylate or 1,8-diazabicyclo[5.4.0]-7-undecene in solvents such as acetonitrile, dimethyl sulphoxide or tert-butanol at a temperature of 25° C. to 100° C. (preferably 25° C. to 60° C.) according to D. E. O'Connors and W. I. Lyness, J. Amer. Chem. Soc. (1964), 86, 3044, or T. Kobayashi et al., Chemistry Letters (1987), 1209; the dialkyl (or aryl) aryl- (or alkyl-)sulphonomethylphosphonates of formula (VIII) or the dialkyl (or aryl) aryl- (or alkyl-)sulphinomethylphosphonates of formula (IX) are prepared by oxidation of dialkyl (or aryl) aryl- (or alkyl-)thiomethylphosphonates according to the methods described in method B.

Dialkyl (or aryl) aryl- (or alkyl-)thiomethylphosphonates are prepared by an Arbuzov reaction of chloromethyl aryl (or alkyl) sulphides with the corresponding trialkyl (or aryl) phosphite (J. March, ibid. p. 848) according to known methods.

Chloromethyl aryl (or alkyl) sulphides are prepared by chloromethylation of the corresponding thiols according to known methods.

Method E

The compounds of formula (I) in which A is ($A_1$) and n=2, the other substituents having the same definition as that shown in the general definition of the invention, can be obtained, in a first stage, by bringing the anion or dianion of a methyl aryl or alkyl sulphone of formula:

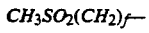   IIIB f and B having the same definition as that shown in the general definition of the invention, into contact with an acetophenone or an acetylpyridine of formula (VI) in which W is methyl and Ar, $R_1$ and m or p have the same definition as in the general definition of the invention, to give the compounds of formula:

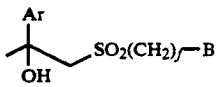   XI in which Ar, $R_1$, m or p, f and B have the same meaning as in the general definition of the invention.

The reaction is carried out in a molar ratio VI:IIIB which is generally between 1 and 5 (preferably 1 and 2), in an aprotic solvent such as tetrahydrofuran at temperature of −70° C. to 50° C. (preferably −70° C. to 20° C.) according to N. Hanack and K. Laping, Tetrahedron Letters (1977), 4493 or D. F. Tavares and P. F. Vogt, Can. J. Chem. (1967), 45, 1519.

The anions of the compounds of formula (IIIB) are prepared by reaction of one or more equivalents of an organometallic compound such as butyllithium or alkylmagnesium halides with the corresponding compounds.

The compounds of formula (I) in which A is ($A_1$) and n=2 are obtained in a second stage, by dehydration of the compounds of formula (XI) according to the method described in method A for the dehydration of the compounds of formula (V).

The dehydration yields a mixture of compounds of formula (I) in which A is ($A_1$) and n=2, and of compounds of formula (X), which can be isomerized in a basic medium according to the method described in method D to give the compounds of formula (I) in which A is (A) and n=2.

The methyl aryl or alkyl sulphones of formula (IIIB) are prepared by reaction of an aryl or alkyl sulphinate of formula (III) with methyl iodide or by oxidation of the corresponding methyl aryl or alkyl sulphides prepared by reaction of an aryl or alkyl thiolate of formula (VIII) with methyl iodide according to the methods described in methods A and B.

The methyl aryl sulphones of formula (IIIB) can also be prepared by direct methylsulphonylation of the corresponding aromatic nucleus, using methylsulphonyl chloride in the presence of methanesulphonic acid and trifluoromethanesulphonic acid according to M. Ono et al., Chem. Letters (1988), 395.

Method F

The compounds of formula (I) in which A is ($A_3$), Y is Cl or Br, and Z is H, the other substituents having the same definition as that shown in the general definition of the invention, can be obtained by halogenation in an aqueous medium of the compounds of formula (I) where A is ($A_1$), obtained previously. The halogenating agents are the N-halosuccinimide or the N-haloacetamide in a molar ratio I:halogenating agent of 1 to 10 (preferably 2 to 4) in a mixture in a proportion of 5/95 to 90/10 (preferably 5/95 to 20/80) of water and of a water-soluble solvent such as dimethyl sulphoxide, dioxane, acetone and others, at a temperature of 0° C. to 60° C. (preferably 20° C. to 40° C.) in the presence or absence of a buffer which may be, for example, acetic acid/sodium acetate, according to H.0. House, J. Amer. Chem. Soc. (1955), 77, 3070 or J. March, ibid. p. 726-727.

Method G

The compounds of formula (I) in which A is ($A_3$), Y is Cl, Br or I, and Z is H, can be prepared by nucleophilic substitution of the compounds of formula (I) in which A is ($A_3$), Y is $OSO_2R_2$, Cl or Br, and Z is H, using the alkali metal (sodium, potassium, lithium) halide salt (Y=Cl, Br, I) in a molar ratio I:salt of 1 to 10 (preferably 1 to 3) in solvents such as acetone, methyl ethyl ketone, glyme, diglyme or dimethylformamide, at a temperature of 25° C. to 180° C. (preferably 40° C. to 160° C.) according to J. March, ibid. p. 381-382.

Method H

The compounds of formula (I) in which A is ($A_3$), Y is Cl or Br, Z is H and n=2, the other substituents having the same definition as that shown in the general definition of the invention, can be prepared by bringing the anion of a methyl aryl or alkyl sulphone of formula (IIIB), f and B having the same definition as that shown in the general definition of the invention, into contact with an ω-haloacetophenone or haloacetylpyridine of formula:

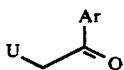

in which U is a chlorine or bromine atom, Ar, $R_1$, m or p having the same definition as that shown in the general definition of the invention, in a molar ratio XII:IIIB which is generally between 1 and 5 (preferably 1 and 2), in an aprotic solvent such as tetrahydrofuran or dimethoxyethane at a temperature of $-100°$ C. to $0°$ C. (preferably $-70°$ C. to $-20°$ C.) according to the references described in method E.

The anions of the compounds of formula (IIIB) and the compounds of formula (IIIB) are prepared according to the methods described in method E.

The compounds of formula XII are prepared according to methods which are known per se.

Method I

The compounds of formula (I) in which A is ($A_3$), Y is Br or Cl, and Z is H, the other substituents having the same definition as that shown in the general definition of the invention, can be prepared by opening of the compounds of formula (I) in which A is ($A_2$), X is 0, the other substituents having the same definition as that shown in the general definition of the invention, by the action of a reactant which gives a halide $Y^-$, Y being the chlorine or bromine atom, such as the hydrogen halide acids HY, the magnesium halide $MgY_2$ and the complexes $NiLi_2Y_4$, according to R. D. Dawe, T. F. Molinski and J. V. Turner, Tetrahedron Letters (1984), 25, 2061, or J. March, ibid., p. 385–386.

Method J

The compounds of formula (I) in which A is ($A_3$), Y is Br or Cl, and Z is ester, the other substituents having the same definition as that shown in the general definition of the invention, can be prepared by halogenation, using the N-halosuccinimide or the N-haloacetamide, of the compounds of formula (I) where A is ($A_1$), obtained previously, in the presence of an acid $R_{11}CO_2H$, $R_{11}$ having the same definition as that shown in the general definition of the invention, in a molar ratio I:halogenating agent of 1 to 10 (preferably 1 to 3), in a mixture in a proportion of 100/0 to 10/90 (preferably 100/0 to 50/50) of acid and of a solvent such as acetone, dioxane and others at a temperature of $0°$ C. to $60°$ C. (preferably $0°$ C. to $20°$ C.) in the presence or absence of the acid salt $R_{11}CO_2M$, M being the sodium, potassium or lithium atom, in a molar ratio I:acid salt of 1 to 10 (preferably 5) according to V. L. Heasley and R. A. Skidgel, J. Org. Chem. (1974), 89, 3953.

The compounds of formula (I) in which A is ($A_3$), Y is I, and Z is ester, can be prepared by nucleophilic substitution of the compounds of formula (I) where A is ($A_3$), Y is Br, and Z is ester, according to the method described in method G.

Method K

The compounds of formula (I) in which A is ($A_3$), Y is $OSO_2R_2$, and Z is H, the other substituents having the same definition as that shown in the general definition of the invention, can be obtained by reaction of the halide $R_2SO_2$-Hal (Hal being preferably the chlorine atom) with the diol compound of formula:

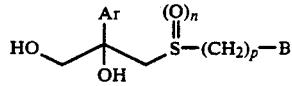

in the presence of a nitrogenous base such as pyridine or triethylamine in a molar ratio XII:halide:base of between 1:1:1 and 1:5:100 (preferably 1:1:1 and 1:2:5) in a solvent such as ether, dimethoxyethane, tetrahydrofuran and others, according to J. March, ibid. p. 357–358.

The compound of formula (XIII) can be prepared by perhydroxylation of the compounds of formula (I) where A is ($A_1$) (n=1, 2) according to known methods (J. March, ibid. p. 732–734) such as, for example, the catalytic action of osmium tetraoxide in the presence of an oxidizing agent such as tert-butyl hydroperoxide in an inert solvent such as acetone or other, in the presence or absence of an ammonium salt, according to Akaski, R. E. Palermo and K. B. Sharpless, J. Org. Chem. (1978), 43, 2063.

Method L

The compounds of formula (I) in which A is ($A_2$), X is 0, the other substituents having the same meaning as that shown in the general definition of the invention, can be obtained by ring closure of a compound of formula (I) where A is ($A_3$) and Y is Cl, Br or I, and Z is H, in the presence of a silver salt $Ag_2O$ in a molar ratio I:$Ag_2O$ of between 1 and 5 (preferably 2 and 3) in an aprotic solvent such as ether, tetrahydrofuran or dimethoxyethane at a temperature of $25°$ C. to $150°$ C. (preferably $60°$ C. to $85°$ C.) according to J. D. McClure, J. Org. Chem. (1967), 32, 3888.

In the case where n=0 or 1, these same compounds of formula (I) in which A is ($A_2$) can also be prepared by ring closure of the compounds of formula (I), where A is ($A_3$), Y is Cl, Br, I or $OSO_2R_2$, and Z is H, in a basic medium (NaOH, KOH, $K_2CO_3$ and others) according to J. March, ibid. p. 343.

The compounds of formula (I) where A is ($A_2$) and n=2 or 1 can be prepared by oxidation of the compounds of formula (I) where A is ($A_2$) and n=1 or 0 according to the methods described in method B.

Method M

The compounds of formula (I) in which A is ($A_2$), n=2, and X=0, the other substituents having the same meaning as that shown in the general definition of the invention, can be obtained by oxidation of a compound of formula (I) where A is ($A_1$), n=2, using oxidizing agents such as organic peracids in a molar ratio I:oxidizing agent of between 1 and 10 (preferably 1 to 3) in a medium buffered with the alkali metal or alkaline-earth metal salt of an organic acid, according to J. March, ibid. p. 735–736.

Method N

The compounds of formula (I) where A is ($A_2$) and X=0, the other substituents having the same meaning as that shown in the general definition of the invention, can be prepared by dehydration of the compounds of formula (XIII) using dehydrating agents such as dimethylacetaldimethylformamide or the diethyl azodicarboxylate/triphenylphosphine reagent according to C. Cortez and R. G. Harvey, Org. Synth. (1978), 58, 12, or J. T. Carlock and M. P Mack, Tetrahedron Letters (1978), 5153.

Method O

The compounds of formula (I) where A is (A$_2$) and X is S, the other substituents having the same definition as that shown in the general definition of the invention, are prepared by reaction of the compounds of formula (I) where A is (A$_2$) and X is O with an alkali metal (generally potassium) thiocyanate salt of 1 to 10 equivalents (preferably 1 to 3) in solvents such as ethanol, acetonitrile and others at temperatures of 25° C. to 120° C. (preferably 25° C. to 60° C.), according to Org. Synth., IV, 232.

These same compounds can also be prepared according to many other known methods according to J. March, ibid. p. 362.

Another subject of the invention is the new products II to XIII which can be used for making use of the process just described.

The following examples illustrate the invention:

EXAMPLE 1 (according to process A)

2-Phenyl-1-propene (130 cc, 1 mole) is dissolved in methylene chloride (1,500 cc). Water (300 cc) and calcium hypochlorite at a concentration of 70% as active chlorine (101.5 g, 0.5 mole) are added. Solid carbon dioxide is added for 2 h with very energetic stirring. The two phases are separated and the organic phase is dried over MgSO$_4$. After evaporation, a yellow oil (145 g) is obtained. NMR analysis (60 MHz) shows the presence of 1-chloro-2-phenyl-2-propene (45%), 1-chloro-2-phenyl-1-propene (45%) and 1-chloro-2-phenyl-2-propanol (10%).

This mixture (17 g, 0.05 molar as 1-chloro-2-phenyl-2-propene) is dissolved in DMF (100 cc). Sodium benzenesulphinate (8.2 g, 0.05 mole) is added and the mixture is heated to 70° C. for 2 h. The reaction mixture is poured into water and ice (350 g). It is stirred energetically with pentane (150 cc) to extract the 1-chloro-2-phenyl-1-propene and the 1-chloro-2-phenyl-2-propanol which have not reacted, for 15 to 30 min until crystallization is complete. The crystals formed are filtered off, are washed with pentane (50 cc) and with diisopropyl ether (50 cc) and are thoroughly drained and dried. 2-Phenyl-1-phenylsulphonyl-2-propene (9.8 g, 76%) is obtained. Mp=105° C.

EXAMPLE 2 (according to process A)

A 0.79 molar ether solution (270 cc) of the 1:1 cyclopropyllithium/lithium bromide complex is added dropwise to condensed sulphur dioxide (240 g) at −70° C.

When the addition is finished, the mixture is allowed to return gradually to ambient temperature with energetic stirring to remove the excess sulphur dioxide. The solid is filtered off, washed with ether (2×100 cc), thoroughly drained and dried. Lithium cyclopropylsulphinate (31 g, 74%) (containing 1 molar equivalent of lithium bromide) is obtained as a hygroscopic white solid.

1-Chloro-2-phenyl-2-propene (10.2 g, 0.05 molar as chloride) prepared according to Example 1 is dissolved in NMP (100 cc). Lithium cyclopropylsulphinate (10 g, 0.05 molar as sulphinate) is added and the mixture is heated to 70° C. for 2 h. The mixture is treated in a manner identical with Example 1 to give brown crystals (8.9 g). After recrystallization from ethanol, white crystals of 1-cyclopropylsulphonyl-2-phenyl-2-propene (4.7 g, 42%) are obtained. Mp=76° C.

EXAMPLE 3 (according to process A)

2-Fluoroaniline (11.1 g, 0.1 mole) is charged and 30% strength sulphuric acid (300 cc) is added. Sodium nitrite (8.3 g, 0.12 mole) dissolved in water (40 cc) is added dropwise at 0° C. The mixture is stirred at 0° C. for 30 min until the salts have dissolved completely.

Concentrated sulphuric acid (50 cc) is added, followed by water (150 cc) and sulphur dioxide (100 g) is introduced gradually at 0° C. Activated copper powder (10 g) is then added portionwise at 0° C. until gas evolution has ceased. The solution is filtered, the precipitate is taken up with a 10% solution of sodium carbonate (200 cc) and is then refiltered. The filtrate is acidified at 0° C. with concentrated sulphuric acid (10 cc) and is reextracted with ether (2×200 cc) and evaporated cold to give sulphinic acid (4.5 g). This is neutralized with normal sodium hydroxide (28 cc) and is dried to obtain sodium 2-fluorobenzenesulphinate (4.9 g, 27%).

1-Chloro-2-phenyl-2-propene (8.24 g, 0.027 molar as chloride) prepared according to Example 1 is dissolved in DMF (150 cc). Sodium 2-fluorobenzenesulphinate (4.9 g, 0.027 mole) is added and the mixture is heated to 70° C. for 2 h. The mixture is heated in a manner identical with Example 1 to give, after recrystallization from ethanol, brown crystals of 1-(2'-fluorophenylsulphonyl)-2-phenyl-2-propene (4.1 g, 55%). Mp=84° C.

EXAMPLE 4 (according to process A)

2-(3'-Dichloro-2'-pyridyl)-1-propene (15.3 g, 0.1 mole) is dissolved in 1,2-dichloroethane (200 cc). Bis(4-chlorophenyl) diselenide (0.5 g, catalyst) and N-chlorosuccinimide (14.7 g, 0.11 mole) are added and the mixture is heated to 60° C. for 24 hours. The reaction mixture is concentrated to a third, the succinimide is filtered off, and the organic phase is washed with water (2×200 cc), with a 15% strength solution of sodium bicarbonate (200 cc) and with water (2×200 cc) and is dried over MgSO$_4$. Crude: 13.9 g.

NMR analysis (60 MHz) shows the presence of 1-chloro-2-(3,-chloro-2,-pyridyl)-2-propene (55%) and 1-chloro-2-(3,-chloro-2,-pyridyl)-1-propene (45%).

In a manner which is identical with the preparation of 2-phenyl-1-phenylsulphonyl-2-propene, this mixture (7 g, 0.02 molar as 1-chloro-2-(3,-chloro-2'-pyridyl)-2-propene)) is treated with sodium benzenesulphinate to obtain, after treatment, 2-(3'-chloro-2'-pyridyl)-1-phenylsulphonyl-2-propene (4.3 g, 73%). Mp=135° C.

EXAMPLE 5 (according to process B)

Potassium carbonate (4.6 g, 0.033 mole) is suspended in acetone (100 cc) and the whole is heated to 50°-60° C. An acetone (30 cc) solution of 2-chlorothiophenol (4.3 g, 0.03 mole) and of a mixture (9.1 g, 0.03 mole) containing 1-chloro-2-phenyl-2-propene (50%) and 1-chloro-2-phenyl-1-propene (50%) is added dropwise under nitrogen. After 1 h of stirring at 50°-60° C. the reaction mixture is poured into water and ice (150 g) and is then reextracted with ether (3×100 cc). It is washed with water (2×150 cc) and dried over MgSO$_4$. The crude (11.7 g) is distilled in a ball oven to give 1-[2'-chlorophenylthio]-2-phenyl-2-propene (6.3 g, 80%) Bp$_{0.5}$=180° C. n$_D^{24}$=1.6340.

EXAMPLE 6 (according to process B)

1-[2'-Chlorophenylthio]-2-phenyl-2-propene (1.56 g, 0.006 mole) is dissolved in methylene chloride (50 cc) and cooled to 0° C. 55% strength mCPBA (1.9 g, 0.006 mole) in solution in methylene chloride (15 cc) is added dropwise over 30 min. After 1 hour at 0° C. the solution is washed with saturated sodium bicarbonate (75 cc), brine (2×75 cc) and is dried over MgSO$_4$. The crude (1.6 g) is chromatographed on silica to give 1-[2'-chlorophenylsulphinyl]-2-phenyl-2-propene (1.0 g, 60%) in the form of an oil. $n_D^{25}$=1.6250.

EXAMPLE 7 (according to process B)

In the same way as in Example 6, 1-[2'-chlorophenylthio]-2-phenyl-2-propene (2.6 g, 0.01 mole) is treated with 55% strength mCPBA (6.9 g, 0.022 mole) with stirring at ambient temperature for 2 h. After the same treatment, the crude (2.6 g) is chromatographed on silica to give 1-[2'-chlorophenylsulphonyl]-2-phenyl-2-propene (1.4 g, 48%) in the form of an oil. $n_D^{22}$=1.6090.

EXAMPLE 8 (according to process B)

Potassium carbonate (27 g, 0.19 mole) is suspended in acetone (600 cc). The mixture is heated to 60° C. and is degassed with nitrogen. A mixture of benzyl mercaptan (21.7 g, 0.17 mole) and (59 g, 0.17 molar as 1-chloro-2-phenyl-2-propene prepared according to Example 4) dissolved in acetone (175 cc) is added dropwise at 60° C. The mixture is heated to 60° C. for two hours.

The reaction mixture is poured into water and ice (2000 g), and is reextracted with ether (3×500 cc). The organic phase is washed with water until neutral and is dried over MgSO$_4$.

Evaporation leaves a yellow oil (82.5 g), which is chromatographed on silica (eluent: heptane followed by 99/1 heptane/chloroform) to give 1-benzylthio-2-phenyl2-propene (19.5 g, 46%). Colourless oil. $n_D^{25}$=1.6041.

1-Benzylthio-2-phenyl-2-propene (13.2 g, 0.055 mole) is dissolved in methanol (300 cc) and water (300 cc). Oxone (36.9 g, 0.12 molar as KHSO$_5$) is added portionwise and stirred for three hours at ambient temperature. The reaction mixture is diluted with water (1,000 cc), pentane (100 cc) is added and the mixture is stirred energetically until crystallization takes place. White crystals of 1-benzylsulphonyl-2-phenyl-2-propene (10.7 g, 72%) are obtained by filtration followed by drying. Mp=118° C.

EXAMPLE 9 (according to process C)

2-Phenyl-1-propene (6.5 cc, 0.05 mole) is dissolved in acetone (200 cc.). Sodium benzenesulphinate (8.2 g, 0.05 mole) is added. Iodine (12.7 g, 0.05 mole) is then added gradually and the mixture is left stirred for 3 days at ambient temperature. The acetone is evaporated off and the residue is taken up with ether (300 cc). It is washed with a 10% strength solution of sodium sulphite (100 cc), 5% strength sodium bicarbonate (100 cc) and water (100 cc) and is dried over MgSO$_4$.

Chromatography on silica yields 2-phenyl-1-phenylsulphonyl-2-propene (3.1 g, 24%). Mp=106° C.

EXAMPLE 10 (according to process D)

A 50:50 mixture of 1-[4,-methylphenylsulphonyl]-2-phenyl-1-propene and of 1-[4,-methylphenylsulphonyl]-2-phenyl-2-propene (2.7 g, 0.01 mole) is dissolved in acetonitrile (10 cc). DBU (3 g, 0.02 mole) is added and the mixture is stirred at ambient temperature for 17 h. The reaction mixture is poured into water (100 g), is reextracted with ether (3×50 cc), the organic phase is washed with 1N hydrochloric acid (2×50 cc) and then water (2×50 d is dried over MgSO$_4$.

NMR analysis (60 MHz) shows an 85:15 ratio of allyl:vinyl sulphone. A recrystallization of the crude (2.4 g) from ether yields pure 1-[4'-methylphenylsulphonyl]-2-phenyl-2-propene (1.3 g, 48%). Mp=103° C.

EXAMPLE 11 (according to process E)

Methyl phenyl sulphone (15.6 g, 0.1 mole) dissolved in THF (100 cc) is added at ambient temperature to a molar solution (100 cc) of ethylmagnesium bromide. The mixture is stirred for 1 h until gas evolution ceases. 2-Acetylpyridine (12.1 g, 0.1 mole) in THF (100 cc) is run in and stirred for 3 h at ambient temperature. The mixture is poured into water (100 cc) and ammonium chloride (10 g) and the two phases are separated. The aqueous phase is acidified and reextracted with ether. The ether phase is set aside. The aqueous phase is adjusted to a basic pH and is reextracted with ether (3×100 cc) and dried over MgSO$_4$.

Evaporation leaves a crude (16 g), which is chromatographed (eluent: CH$_2$Cl$_2$, followed by 95/5 CH$_2$Cl$_2$/acetone) to give white crystals of 1-phenylsulphonyl-2-(2,-pyridyl)-2-propanol (8.3 g, 30%). Mp=99° C.

1-Phenylsulphonyl-2-(2,-pyridyl)-2-propanol (2.8 g, 0.01 mole) is dissolved in pyridine (15 cc). Thionyl chloride (1.3 g, 0.11 mole) is added and stirred for 1 day at ambient temperature. The pyridine is evaporated off and the residue is taken up with methylene chloride (25 cc), washed with water (3×25 cc) and dried over MgSO$_4$.

The solution is filtered, absorbed onto silica and chromatographed as above to give the allyl isomer: crystals of 1-phenylsulphonyl-2-(2=-pyridyl)-2-propene (1.6 g, 62%). Mp=80° C.

EXAMPLE 12 (according to process E)

Thionyl chloride (14.5 cc, 0.2 mole) is dissolved in methanesulphonic acid (33.2 cc, 0.51 mole) and heated under reflux for 1 h. The solution is cooled to 25° C., 1,3-dichlorobenzene (15 g, 0.1 mole) is added, followed by trifluoromethanesulphonic acid (0.9 cc, 0.01 mole), and the mixture is heated to 120° C. for 3 h. It is cooled, poured onto water and ice (200 g), is reextracted with ethyl acetate (2×150 cc), and the organic phase is washed with water (3×200 cc) and is dried over MgSO$_4$.

The crystallized crude (27 g) is recrystallized from a ⅓ ethyl acetate/heptane mixture to give white crystals of methylsulphonyl(2,4-dichlorobenzene) (11.7 g, 51%). Mp=71° C.

In a manner identical with Example 11, methylsulphonyl(2,4-dichlorobenzene) (6 g, 0.026 mole) is condensed with acetophenone (3.2 g, 0.026 mole) to obtain, after chromatography, white crystals of 1-(2',4'-dichlorophenylsulphonyl)-2-phenyl-2-propanol (2.1 g, 23%). Mp=94° C.

In a manner identical with Example 11, 1-(2',4'-dichlorophenylsulphonyl)-2-phenyl-2-propanol (3.2 g, 0.009 mole) is treated with thionyl chloride (1.1 g, 0.009 mole) in pyridine, for 30 min at 20° C. After treatment and chromatography, the vinyl isomer (1.1 g) and the allyl isomer are obtained; a colourless oil (0.7 g, 21%) of 1-(2',4'-dichlorophenylsulphonyl)-2-phenyl-2-propene.

The following compounds are prepared according to processes A to E:

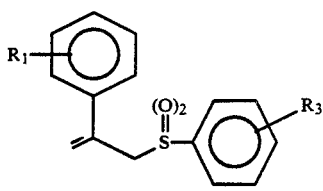

| Example | R₁ | R₃ | Mp (solvent) $n_D$ (temperature) |
|---|---|---|---|
| 13 | 2-F | H | 95° C. (Et₂O) |
| 14 | 3-F | H | 104,5° C. (Et₂O) |
| 15 | 4-F | H | 85° C. (CHCl₃) |
| 16 | 2-Cl | H | $n_D^{25} = 1,5905$ |
| 17 | 3-Cl | H | $n_D^{25} = 1,6000$ |
| 18 | 4-Cl | H | 75° C. (Et₂O) |
| 19 | 4-CH₃ | H | 92° C. (Et₂O) |
| 20 | 4-OCH₃ | H | 60° C. (Et₂O) |
| 21 | 3-OCH₃ | H | $n_D^{25} = 1,5920$ |
| 22 | 3-Br | H | 75° C. (Et₂O) |
| 23 | 3-CF₃ | H | 85° C. (Et₂O) |
| 24 | 2,4-diCl | H | 85° C. (CCl₄) |
| 25 | 3,5-diCl | H | 98° C. (Et₂O/CHCl₃) |
| 26 | 3,4-diCl | H | 85° C. (Et₂O) |
| 27 | 3-F | 2-Cl | $n_D^{26} = 1,5860$ |
| 28 | 3-Cl | 2-Cl | 87° C. (chromatography) |
| 29 | 3-F | 2-F | porous solid |
| 30 | 3,5-diCl | 2-Me | 72° C. (EtOH) |
| 31 | 3,5-diCl | 2-Cl | 94° C. (EtOH) |
| 32 | 3-CF₃ | 2-Me | 51° C. (EtOH) |
| 33 | 3-CF₃ | 2-Cl | 50° C. (chromatography) |
| 34 | H | 2-OCH₃ | $n_D^{23} = 1,5910$ |
| 35 | H | 2-Br | $n_D^{22} = 1,5775$ |
| 36 | H | 3-F | 70° C. (ET₂O) |
| 37 | H | 4-F | 83° C. (chromatography) |
| 38 | H | 3-Cl | 71,5° C. (chromatography) |
| 39 | H | 4-Cl | 114° C. (Et₂O/CHCl₃) |
| 40 | H | 2-CH₃ | 62° C. (EtOH) |
| 41 | H | 3-CH₃ | 61° C. (EtOH) |
| 42 | H | 2,4-diCH₃ | 63° C. (chromatography) |
| 43 | H | 2,6-diCl | $n_D^{25} = 1.6125$ |
| 44 | H | 2-Cl 4-F | 64° C. (Et₂O/CHCl₃) |
| 45 | H | 4-Br | 133° C. (chromatography) |

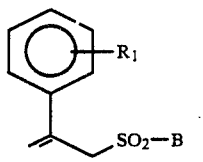

| Example | R₁ | B | Mp (solvent) $n_D$ (temperature) |
|---|---|---|---|
| 46 | H | CH₃ | $n_D^{25} = 1,5695$ |
| 47 | H | CH(CH₃)₂ | $n_D^{25} = 1,55570$ |
| 48 | H | (CH₂)₃CH₃ | 25° C. (chromatography) |
| 49 | 3-Cl | cyclopropyl | 51° C. (EtOH) |
| 50 | H | 2-pyridyl | 45° C. (chromatography) |
| 51 | H | cyclopentyl | $n_D^{23} = 1,5675$ |
| 52 | 3-Cl | CH(CH₃)₂ | $n_D^{23} = 1,5715$ |

EXAMPLE 53 (according to process F)

2-Phenyl-1-phenylsulphonyl-2-propene (5.2 g, 0.02 mole) is dissolved in DMSO (50 cc) and water (10 cc). N-bromosuccinimide (11.1 g, 0.06 mole) is added portionwise and stirred for 4 days at ambient temperature. The reaction mixture is poured into water and ice (350 g) and is stirred energetically with pentane (100 cc) for 15 min. The crystals are filtered off, washed with pentane (2×50 cc) and recrystallized from an ether/chloroform mixture to give flocculent white crystals of 1-bromo-2-phenyl-3-phenylsulphonyl-2-propanol (3 g, 42%). Mp=91° C.

EXAMPLE 54 (according to process F)

2-[3'-Bromophenyl]-1-phenylsulphonyl-2-propene (1.7 g, 0.005 mole) is dissolved in acetone (50 cc). Sodium acetate (0.6 g), water (12.5 cc) and acetic acid (12.5 cc) are added. N-Bromoacetamide (1.4 g, 0.01 mole) is added portionwise and stirred for 3 h at ambient temperature. The mixture is poured into water (150 cc), reextracted with ether (3×100 cc), the organic phase is washed until neutral and is dried over MgSO₄. The crystallized crude (2.3 g) is recrystallized from carbon tetrachloride to give yellow crystals of 1-bromo-2-[3'-bromophenyl]-3-phenylsulphonyl-2-propanol (0.9 g, 40%). Mp=134° C.

EXAMPLE 55 (according to process F)

1-[2'-Bromophenylthio]-2-phenyl-2-propene (2.1 g, 0.007 mole) is dissolved in dimethyl sulphoxide (10 cc) and water (2.5 cc) is added. N-Bromosuccinimide (1.5 g, 0.008 mole) is added portionwise at 0° C. and stirred for 1 h 30 min at 0° C. The mixture is poured into water (100 cc), reextracted with ether (2×100 cc) and the ether phase is washed and then dried over MgSO₄.

The oily crude (1.7 g) is precipitated with pentane to give, by filtration, yellow crystals of 1-bromo-3-[2'-bromophenylthio]-2-phenyl-2-propene (1.4 g, 50%). Mp=65° C.

In a manner identical with Example 8, 1-bromo-3-[2'-bromophenylthio]-2-phenyl-2-propene (1.1 g, 0.003 mole) is treated with Oxone (2.5 g) to obtain, after recrystallization from a 4/1 ether/chloroform mixture, white crystals of 1-bromo-3-[2'-bromophenylsulphinyl]-2-phenyl-2-propene (0.6 g, 51%). Mp=134° C.

EXAMPLE 56 (according to process G)

1-Bromo-2-phenyl-3-phenylsulphonyl-2-propanol (1.3 g, 0.004 mole) is dissolved in acetone (30 cc). Sodium iodide (0.9 g, 0.006 mole) is added and heated under reflux for 15 h. The reaction mixture is poured into water (100 cc), reextracted with ether (3×50 cc), washed with a 15% strength NaHSO₃ solution (50 cc) and then with water (50 cc) and is dried over MgSO₄. The crystallized crude (0.9 g) is recrystallized from carbon tetrachloride to give yellow crystals of 1-iodo-2-phenyl-3-phenylsulphonyl-2-propanol (0.5 g, 31%). Mp=98° C.

EXAMPLE 57 (according to process H)

Methyl phenyl sulphone (12.5 g, 0.08 mole) dissolved in THF (150 cc) is added at ambient temperature to a molar solution (100 cc) of ethylmagnesium bromide. The mixture is stirred for 1 h and then cooled to −50° C. 2-Chloroacetophenone (12.5 g, 0.08 mole) dissolved in THF (150 cc) is run in and stirred for 2 h at −20° C. The mixture is poured into normal hydrochloric acid (200 cc) and ammonium chloride (6 g). It is reextracted with ether (3×50 cc), washed until neutral and dried over MgSO₄. The crude is precipitated with heptane and recrystallized from isopropyl ether to give flocculent white crystals of 1-chloro-2-phenyl-3-phenylsulphonyl-2-propanol (6.5 g, 26%). Mp=110° C.

EXAMPLE 58 (according to process H)

In a manner identical with Example 57, 2,3'-dibromoacetophenone (7.8 g, 0.028 mole) is treated with 1 equivalent of the magnesium anion of methyl phenyl sulphone in THF at −70° C. The mixture is stirred for 2 h at −70° C., acetic acid (7 cc) is then added and the mixture is poured into water (100 g). It is reextracted with ether (3×100 cc), is washed with brine (2×100 cc) and is dried over MgSO4. The crude is precipitated with ether (50 cc) with warming and recrystallized from isopropyl ether to give white crystals of 1-bromo-2-[3'-bromophenyl]-3-phenylsulphonyl-2-propanol (2.4 g, 20%). Mp=132° C.

EXAMPLE 59 (according to process I)

2-[2'-Chlorophenylsulphonylmethyl]-2-[3'-fluorophenyl]oxirane (0.8 g 0.0025 mole) is dissolved in THF 0° C. and stirred for 2 h at ambient temperature. A buffer solution (12 cc) at a pH equal to 7 is added, the mixture is reextracted with methylene chloride (3×50 cc) and the solution is dried over MgSO4. Evaporation leaves an oil (1.0 g), which is chromatographed (eluent: 80/20 heptane/chloroform) to give white crystals of 1-bromo-3-- [2'-chlorophenylsulphonyl]-2-[3'-fluorophenyl]-2-propanol (0.7 g, 68%). Mp=121° C.

EXAMPLE 60 (according to process J)

2-Phenyl-1-phenylsulphonyl-2-propene (2.6 g, 0.01 mole) is suspended in acetic acid (50 cc). Sodium acetate (4.1 g, 0.05 mole) is then added, followed by N-bromosuccinimide (3.6 g, 0.02 mole) and the mixture is stirred for 3 h at ambient temperature. The mixture is then poured into water and ice (200 g) and stirred energetically until a resin forms. The resin is filtered off, redissolved in methylene chloride (50 cc), and is washed with a 10% strength sodium bicarbonate solution (100 cc), water (2×100 cc), and is dried over MgSO4. Evaporation leaves a yellow oil (3.5 g). This oil is dissolved in an ether/chloroform mixture (10 cc) and stored overnight at −18° C.

After filtration, yellow crystals of 2-acetoxy-1-bromo-2-phenyl-3-phenylsulphonylpropane (2.3 g, 59%) are obtained. Mp=103° C.

EXAMPLE 61 (according to process J)

In a manner identical with Example 60, 2-phenyl-1-phenylsulphonyl-2-propene (2.6 g, 0.01 mole) is treated with N-bromosuccinimide (1.8 g, 0.01 mole) in trifluoroacetic acid in the presence of sodium trifluoroacetate (6.8 g, 0.05 mole). After treatment, evaporation leaves an oil (4 g), which is crystallized from ether (10 cc) overnight at −18° C. White crystals of 1-bromo-2-trifluoroacetoxy-2-phenyl-3-phenylsulphonylpropane (2.1 g, 47%) are filtered off. Mp=100° C.

EXAMPLE 62 (according to process K)

2-Phenyl-1-phenylsulphonyl-2-propene (5.16 g, 0.02 mole) is dissolved in acetone (40 cc). Tetrabutylammonium acetate (1.3 g, 0.005 mole) and 70% strength tert-butyl hydroperoxide (4.4 cc, 0.03 mole) are added and the mixture is stirred at ambient temperature for 15 h.

Ether (80 cc) is added, the mixture is cooled to 0° C. and a 10% strength NaHSO3 solution (10 cc) is added in one lot. After 1 h stirring, the two phases are separated, the aqueous phase is saturated with NaCl (4 g) and is reextracted with ether (2×25 cc) and the combined organic phases are washed with brine (50 cc) and dried over MgSO4.

The crystallized crude (5.5 g) is recrystallized from acetone to give white crystals of 2-phenyl-3-phenylsulphonyl-1,2-propanediol (3.6 g, 61%). Mp=137° C.

2-Phenyl-3-phenylsulphonyl-1,2-propanediol (1.3 g, 0.004 mole) is dissolved in pyridine (25 cc) and cooled to 0° C. Methanesulphonyl chloride (0.5 g, 0.005 mole) is added and stirred at ambient temperature for 2 h. The mixture is poured into a mixture of ice (100 g) and 35% strength hydrochloric acid (30 cc) and is stirred energetically with pentane (25 cc). The crystals formed are filtered off, dried and recrystallized from ethyl acetate to give white crystals of 1-methanesulphonate-2-phenyl-3-phenylsulphonyl-2-propanol (0.7 g, 42%). Mp=144° C.

EXAMPLE 63 (according to process L)

1-Bromo-2-phenyl-3-phenylsulphonyl-2-propanol (1.1 g, 0.003 mole) is dissolved in dimethoxyethane (20 cc). Silver oxide Ag2O (1.4 g, 0.006 mole) is added and heated under reflux for 20 h. The mixture is filtered hot through supercel; the cake is washed with methylene chloride (100 cc). The organic phase is dried over MgSO4.

The crystallized crude (0.9 g) is recrystallized from carbon tetrachloride to give yellow crystals of 2-phenyl-2-[phenylsulphonylmethyl]oxirane (0.7 g, 85%). Mp=89° C.

EXAMPLE 64 (according to process N)

In a manner identical with Example 62, 2-[3'-fluorophenyl]-1-[2'-chlorophenylsulphonyl]-2-propene (10.3 g, 0.033 mole) is treated with 70% strength tert-butyl hydroperoxide (7.5 cc, 0.05 mole) in the presence of tetrabutylammonium acetate (1.1 g, 0.008 mole) and osmium oxide catalyst. After treatment and recrystallization from acetone, white crystals of 3-[2'-chlorophenylsulphonyl]-2-[3,-fluorophenyl]-1,2-propanediol (8.7 g, 76%) are obtained. Mp=132° C.

3-[2'-Chlorophenylsulphonyl]-2-[3'-fluorophenyl]-1,2-propanediol (4 g, 0.012 mole) is dissolved in chloroform (75 cc). The solution is cooled to 0° C. and triphenylphosphine (3.2 g, 0.012 mole) is added, followed, dropwise, by diethyl azodicarboxylate (2.8 g, 0.016 mole). The mixture is stirred at ambient temperature for 15 h. The chloroform is evaporated off and the residue is chromatographed (eluent: 50/50 heptane/chloroform) to give white crystals of 2-[2'-chlorophenylsulphonylmethyl]-2-[3,-fluorophenyl]oxirane (2.4 g, 61%). Mp=104° C.

The compounds collated in the tables below were prepared according to methods F to I and K.

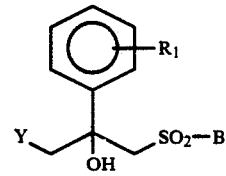

| Example | Y | R1 | B | Mp (solvent) |
|---|---|---|---|---|
| 65 | Br | 3,5-diCl | phenyl | 131° C. (Et2O/CHCl3) |
| 66 | Br | H | 2-Cl phenyl | 140° C. (chromat.) |
| 67 | Br | H | 2-F phenyl | 117° C. (Et2O/CHCl3) |
| 68 | Br | H | 2-CH3 phenyl | 123° C. (Et2O/CHCl3) |
| 69 | Cl | H | 2-Cl phenyl | 131° C. (CH2Cl2/iPr2O) |
| 70 | Br | H | 3-CH3 phenyl | 122° C. (EtOH) |
| 71 | Br | H | 2-Cl, 4-F phenyl | 122° C. (Et2O/CHCl3) |
| 72 | Br | H | CH(CH3)2 | 101° C. (CHCl3) |
| 73 | Cl | H | CH(CH3)2 | 110° C. (iPr2O) |

-continued

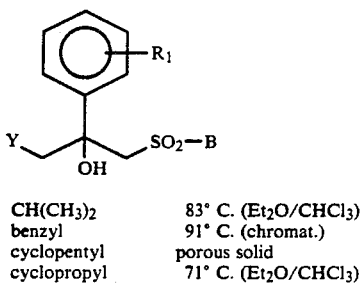

| | | | | |
|---|---|---|---|---|
| 74 | Br | 3-Cl | CH(CH₃)₂ | 83° C. (Et₂O/CHCl₃) |
| 75 | Br | H | benzyl | 91° C. (chromat.) |
| 76 | Br | H | cyclopentyl | porous solid |
| 77 | Br | H | cyclopropyl | 71° C. (Et₂O/CHCl₃) |

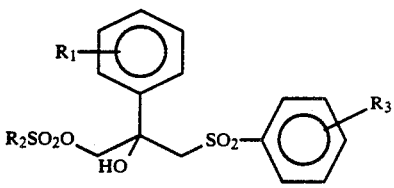

| Example | R₁ | R₂ | R₃ | Mp (solvent) |
|---|---|---|---|---|
| 78 | H | CH₃(CH₂)₂ | H | 112° C. (AcOEt/pentane) |
| 79 | H | (CH₃)₂CH | H | 83° C. (AcOEt) |
| 80 | H | Cl(CH₂)₃ | H | 98° C. (AcOEt/pentane) |
| 81 | 3-Br | CH₃ | H | 147° C. (CH₂Cl₂) |
| 82 | 3-F | CH₃ | 2-Cl | 123° C. (AcOEt) |
| 83 | H | CH₃ | 2-CH₃ | 160° C. (AcOEt) |
| 84 | H | 4-Br phenyl | H | 118° C. |
| 85 | H | 4-OCH₃ phenyl | H | 129° C. (AcOEt/pentane) |
| 86 | H | 4-NO₂ phenyl | H | 116° C. (AcOEt/pentane) |
| 87 | H | 4-CH₃ phenyl | H | 114° C. (AcOEt) |

The invention also relates to the use of the compounds of formula (I) as herbicides. As weeds which can be controlled or destroyed by the compounds of formula (I) there may be mentioned:

| Abbreviations | Latin name | English name |
|---|---|---|
| | Graminaceae/Cyperaceae | |
| AVE | Avena fatua | Wild oat |
| ECH | Echinochloa crusgalli | Panic grass |
| LOL | Lolium multiflorum | Italian ryegrass |
| SOR | Sorghum halepense | Johnson grass |
| ALO | Alopecurus myosuroides | Slender foxtail |
| CYP | Cyperus esculentus | Chufa flat sedge |
| DIG | Digitaria sanguinalis | Hairy fingergrass |
| PAN | Panicum miliaceum | Common millet |
| SET | Setaria faberii | Giant foxtail |
| | Dicotyledons: | |
| IPO | Ipomea purpurea | Common morning glory |
| SIN | Sinapis arvensis | Charlock |
| ABU | Abutilon theophrasti | Indian mallow |
| SOL | Solanum nigrum | Black nightshade |

The use of the compounds of formula (I) is most of the time in the form of a herbicidal composition comprising one or more agriculturally acceptable carriers.

In fact, for their use in practice, the compounds according to the invention are rarely employed by themselves. In most cases these compounds form part of compositions. These compositions, which can be employed as herbicidal agents, contain as an active ingredient a compound according to the invention such as described above, mixed with the agriculturally acceptable solid or liquid carriers, and surface-active agents, also agriculturally acceptable. In particular, the usual inert carriers and the usual surface-active agents can be employed. These compositions also form part of the invention.

These compositions may also contain all kinds of other ingredients such as, for example, protective colloids, adhesives, thickeners, thixotropic agents, penetrating agents, stabilizers, sequestrants, and the like. More generally, the compounds employed in the invention may be combined with any solid or liquid additives corresponding to the usual formulation techniques.

In general, the compositions according to the invention usually contain approximately from 0.05 to 95% (by weight) of a compound according to the invention, one or more solid or liquid carriers and, optionally, one or more surface-active agents.

In this description, the term "carrier" refers to a natural or synthetic, organic or inorganic substance with which the compound is combined to facilitate its application to the plant, to seeds or to the soil. This carrier is therefore generally inert and it must be agriculturally acceptable, especially to the plant which is treated. The carrier may be solid (clays, natural or synthetic silicates, silica, resins, waxes, solid fertilizers, and the like) or liquid (water, alcohols, especially butanol, and the like).

The surface-active agent may be an emulsifying, dispersing or wetting agent of ionic or nonionic type or a mixture of such surface-active agents. For example, there may be mentioned salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of sulphosuccinic acid esters, taurine derivatives (especially alkyltaurates), phosphoric esters of ethylene oxide condensates with alcohols or phenols, esters of fatty acids with polyols, and derivatives of the above compounds containing sulphate, sulphonate and phosphate functional groups. The presence of at least one surface-active agent is generally indispensable when the compound and/or the inert carrier ar not soluble in water and when the application vector agent is water.

Thus, therefore, the compositions for agricultural use according to the invention may contain the active substances according to the invention within very wide limits ranging from $5 \times 10^{-5}\%$ to 95% (by weight). Their surface-active agent content is advantageously between 5% and 40% by weight.

These compositions according to the invention are themselves in fairly diverse, solid or liquid, forms.

Solid forms of composition which can be mentioned are dusting powders (with a content of compound which can be up to 100%) and granulates, particularly those obtained by extrusion, compacting or impregnation of a granular carrier, or granulation starting from a powder (the content of the compound in these granules being between 0.5 and 80% in these latter cases).

The wettable powders (or powder for spraying) are usually prepared so that they contain 20 to 95% of active ingredient, and, in addition to the solid carrier, they usually contain from 0 to 30% of a wetting agent, from 3 to 20% of a dispersing agent and, when necessary, from 0 to 10% of one or more stabilizers and/or other additives, such as penetrating agents adhesives or anticaking agents, colorants, and the like.

To obtain the powders for spraying or wettable powders, the active ingredients are mixed intimately with the additional substances in suitable mixers and are ground using mills or other suitable grinders. This produces powders for spraying whose wettability and formation of a suspension are advantageous; they can be suspended using water at any desired concentration and these suspensions can be employed very advantageously, in particular for the application to plant foliage.

Pastes can be produced in place of wettable powders. The conditions and methods for producing and using these pastes are similar to those for the wettable powders or powders for spraying.

By way of example, here are various compositions of wettable powders (or powders for spraying):

EXAMPLE F 1

| | |
|---|---|
| Active ingredient (Compound no. 1) | 50% |
| Condensate of ethylene oxide with fatty alcohol (wetting agent) | 2.5% |
| Condensate of ethylene oxide with phenylethylphenol (dispersing agent) | 5% |
| Chalk (inert carrier) | 42.5% |

EXAMPLE F2

| | |
|---|---|
| Active ingredient (Compound no. 1) | 10% |
| Branched type $C_{13}$ synthetic oxo alcohol condensed with 8 to 10 ethylene oxides (wetting agent) | 0.75% |
| Neutral calcium lignosulphate (dispersing agent) | 12% |
| Calcium carbonate (inert filler) q.s. | 100% |

EXAMPLE F 3

This wettable powder contains the same ingredients as in the preceding example, in the following proportions:

| | |
|---|---|
| Active ingredient | 75% |
| Wetting agent | 1.50% |
| Dispersing agent | 8% |
| Calcium carbonate (inert filler) q.s. | 100% |

EXAMPLE F 4

| | |
|---|---|
| Active ingredient (Compound no. 1) | 90% |
| Condensate of ethylene oxide with fatty alcohol (wetting agent) | 4% |
| Condensate of ethylene oxide with phenylethylphenol (dispersing agent) | 6% |

EXAMPLE F 5

| | |
|---|---|
| Active ingredient (Compound no. 1) | 50% |
| Mixture of anionic and nonionic surfactants (wetting agent) | 2.5% |
| Sodium lignosulphonate (dispersing agent) | 5% |
| Kaolin clay (inert carrier) | 42.5% |

The compounds according to the invention can be formulated in the form of dry flowables which can be dispersed in water, also included within the scope of the invention.

These dry flowables, with an apparent density which is generally between approximately 0.3 and 0.6, have a particle size which is generally between approximately 150 and 2,000, and preferably between 300 and 1,500 microns.

The content of active ingredient in these granulates is generally between approximately 1% and 90%, and preferably between 25% and 90%.

The remainder of the granulate consists essentially of a solid filler and optionally of surface-active adjuvants endowing the granulate with water-dispersibility properties. These granulates can be essentially of two distinct types, depending on whether the filler chosen is or is not water-soluble. When the filler is water-soluble, it can be inorganic or, preferably, organic. Excellent results have been obtained with urea. In the case of an insoluble filler, the latter is preferably inorganic, such as, for example, kaolin or bentonite. It is then advantageously accompanied by surface-active agents (in a proportion of 2 to 20% by weight of the granulate) more than half of which is, for example, made up of at least one essentially anionic dispersing agent such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Furthermore, other adjuvants, such as foam suppressors, can be added, although this is not essential.

The granulate according to the invention may be prepared by mixing the necessary ingredients followed by granulation by a number of techniques which are known per se (pelletizer, fluid bed, sprayer, extrusion, and the like). The finishing operation is generally a crushing followed by a screening to the chosen particle size within the limits mentioned above.

It is preferably obtained by extrusion, the operation being carried out as shown in the examples below.

EXAMPLE F 6

Dry Flowables

90% by weight of active ingredient (compound no. 1) and 10% of urea prills are mixed in a blender. The blend is then ground in an attritor mill. A powder is obtained, which is moistened with approximately 8% by weight of water. The wet powder is extruded in a perforated-roll extruder. A granulate is obtained, which is dried and then crushed and screened, so as to retain only the granules whose size is between 150 and 2,000 microns respectively.

EXAMPLE F 7

Dry Flowables

The following constituents are mixed in a blender:

| | |
|---|---|
| Active ingredient (Compound no. 1) | 75% |
| Wetting agent (sodium alkylnaphthalene-sulphonate) | 2% |
| Dispersing agent (sodium polynaphthalene-sulphonate) | 8% |
| Water-insoluble inert filler (kaolin) | 15% |

This blend is granulated in a fluid bed, in the presence of water, and is then dried, crushed and screened so a to obtain granules whose size is between 0.15 and 0.80 mm.

These granulates can be employed by themselves, in solution or dispersion in water, so as to obtain the required dosage. They can also be employed to prepare combinations with other active ingredients, especially fungicides, the latter being in the form of wettable powders or of granulates or aqueous suspensions.

The compounds of formula (I) can also be employed in the form of dusting powders; a composition comprising 50 g of active ingredient and 950 g of talc can also be employed; it is also possible to employ a composition comprising 20 g of active ingredient, 10 g of finely divided silica and 970 g of talc; these constituents are blended and ground and the blend is applied by dusting.

As forms of compositions which are liquid or intended to constitute liquid compositions when applied, there may be mentioned solutions, in particular water-soluble concentrates, emulsifiable concentrates, emulsions, flowables, aerosols, wettable powders (or powder for spraying) and pastes.

Emulsifiable or soluble concentrates in most cases contain 10 to 80% of active ingredient, while the emulsions or solutions which are ready for application contain, for their part, 0.001 to 20% of active ingredient.

In addition to the solvent, emulsifiable concentrates can, when necessary, contain 2 to 20% of suitable additives such as the abovementioned stabilizers, surface-active agents, penetrating agents, corrosion inhibitors, colorants or adhesives.

By diluting these concentrates with water it is possible to obtain emulsions of any desired concentration, which are particularly suitable for application to crops.

By way of example, here is the composition of a few emulsifiable concentrates:

EXAMPLE F 8

| Active ingredient | 400 g/l |
|---|---|
| Alkali metal dodecylbenzenesulphonate | 24 g/l |
| 10:1 Ethylene oxide/nonylphenol condensate | 16 g/l |
| Cyclohexanone | 200 g/l |
| Aromatic solvent q.s. | 1 liter |

According to another emulsifiable concentrate formula, the following are employed:

EXAMPLE F 9

| Active ingredient | 250 g |
|---|---|
| Epoxidized vegetable oil | 25 g |
| Mixture of alkylarylsulphonate and of polyglycol ether and of fatty alcohols | 100 g |
| Dimethylformamide | 50 g |
| Xylene | 575 g |

Flowables, which can also be applied by spraying, are prepared so as to obtain a stable fluid product which does not settle, and usually contain from 10 to 75% of active ingredient, from 0.5 to 15% of surface-active agents, from 0.1 to 10% of thixotropic agents, from 0 to 10% of suitable additives, such as foam suppressors, corrosion inhibitors, stabilizers, penetrating agents and adhesives and, as a carrier, water or an organic liquid in which the active ingredient is poorly soluble or insoluble; certain organic solid materials or inorganic salts may be dissolved in the carrier to help to prevent settling, or as antifreezes for water.

By way of example, here is a composition of a flowable:

EXAMPLE F 10

| Compound | 500 g |
|---|---|
| Polycondensate of ethylene oxide with tristyrylphenol phosphate | 50 g |
| Polycondensate of ethylene oxide with an alkylphenol | 50 g |
| Sodium polycarboxylate | 20 g |
| Ethylene glycol | 50 g |
| Organopolysiloxane oil (antifoam) | 1 g |
| Polysaccharide | 1.5 g |
| Water | 316.5 g |

Aqueous dispersions and emulsions, for example the compositions obtained by diluting with water a wettable powder or an emulsifiable concentrate according to the invention, are included within the general scope of the present invention. The emulsions may be of the water-in-oil or oil-in-water type and may be of a thick consistency, such as that of a mayonnaise.

With regard to the compositions which are adapted to storage and to transport, these contain more advantageously from 0.5 to 95% (by weight) of active ingredient.

The present invention also relates to a weeding process (especially of dicotyledon or maize cultivation areas) which consists in applying an effective quantity of a compound of formula (I) to the plants which are to be destroyed.

The products and compositions according to the invention are convenient to apply to vegetation and especially to the weeds to be eliminated when the latter have a green foliage.

Nevertheless, a weeding process will be employed which consists in applying an effective quantity of a compound of formula (I) to the areas or plots where it is desired to prevent the growth or the development of plants which have not yet grown (pre-emergence application).

It is also possible to operate so that the crop is sown before or after treatment.

The application rate of active ingredient is generally between 1 and 8,000 g/ha.

The examples below illustrate the invention:

EXAMPLE A

Herbicidal Application, at Pre-Emergence of Plant Species

A number of seeds, determined depending on the plant species and the size of the seed, are sown in 7×7×8 cm pots filled with light agricultural soil.

The pots are sprayed with a spraying mixture in a quantity corresponding to a volume application rate of 500 l/ha and containing the active ingredient at the required concentration.

The treatment with the spraying mixture is therefore carried out o seeds which are not covered with soil (the term spraying mixture is employed to refer, generally, to water-diluted compositions, in the form in which they are applied to the plants).

The spraying mixture employed for the treatment is a solution or suspension of the active ingredient in an acetone/water mixture in 50/50 proportions, in the presence of 0.05% by weight of Cemulsol NP 10 (surface-active agent) consisting of a polycondensate of ethylene oxide with an alkylphenol, especially a polycondensate of ethylene oxide with nonylphenol) and 0.04% by weight of Tween 20 (a surface-active agent consisting of an oleate of an ethylene oxide polycondensate derivative of sorbitol).

In the case of a suspension, the latter is obtained by blending and milling the ingredients in a micronizer so as to obtain an average particle size smaller than 40 microns.

After treatment, the seeds are covered with a layer of soil approximately 3 mm in thickness.

The pots are then placed in troughs intended to receive the moistening water, by sub-irrigation, and are maintained at ambient temperature and 70% relative humidity for 24 days.

Scoring the Herbicidal Activity

The reading is carried out in the following manner:

After 24 days the destruction of the number of stalks in the treated pot is measured as a percentage (D) relative to the number of plants in the untreated (control) pots. The percentage reduction in size (SR) of the remaining treated plants is measured, relative to the control plants.

The percentage of foliage volume which is not destroyed by the product is therefore given by the formula $$([100-D] \times [100-SR])/100 = A$$

This value A is converted into a score of 0 to 5 according to the following scale:

|  |  |  | Score |  |
|---|---|---|---|---|
| 0 | ≦ A ≦ | 10 | 5 | (complete destruction) |
| 10 | ≦ A ≦ | 30 | 4 |  |
| 30 | ≦ A ≦ | 50 | 3 |  |
| 50 | ≦ A ≦ | 70 | 2 |  |
| 70 | ≦ A ≦ | 90 | 1 |  |
| 90 | ≦ A ≦ | 100 | 0 | (no effect) |

The results obtained are shown after Example B for application dosages of 4,000 g/ha.

EXAMPLE B

Herbicidal Application, at Post-Emergence of the Plant Species

A number of seeds, determined depending on the plant species and the size of the seed, are sown in 7×7×8 cm pots filled with light agricultural soil.

The seeds are then covered with a layer of soil approximately 3 mm in thickness and the seed is left to germinate until it gives rise to a small plant at the appropriate stage The treatment stage for the graminaceous plants is the "second leaf being formed" stage. The treatment stage for the dicotyledon plants is the "cotyledons spread out, first true leaf being developed" stage.

The pots are then sprayed with a spraying mixture in a quantity corresponding to a volume application rate of 500 l/ha and containing the active ingredient at the required concentration.

The spraying mixture was prepared in the same way as in Example 41.

The treated pots are next placed in troughs intended to receive the moistening water, by sub-irrigation, and maintained at ambient temperature and 70% relative humidity for 24 days.

Scoring the Herbicidal Activity

The reading is carried out in the following manner:

After 24 days, the destruction of the number of stalks in the treated pot is measured as a percentage (D) relative to the number of plants in the untreated (control) pots. The percentage reduction in size (SR) of the remaining treated plants is measured, relative to the control plants.

The percentage of foliage volume which is not destroyed by the product is therefore given by the formula $$([100-D] \times [100-SR])/100 = a$$

This value A is converted into a score of 0 to 5 according to the following scale:

|  |  |  | Score |  |
|---|---|---|---|---|
| 0 | ≦ A ≦ | 10 | 5 | (complete destruction) |
| 10 | ≦ A ≦ | 30 | 4 |  |
| 30 | ≦ A ≦ | 50 | 3 |  |
| 50 | ≦ A ≦ | 70 | 2 |  |
| 70 | ≦ A ≦ | 90 | 1 |  |
| 90 | ≦ A ≦ | 100 | 0 | (no effect) |

The results obtained are shown after Example B for application rates of 4,000 g/ha.

The plant species employed in these Examples A and B are:

| Abbreviations | Latin name | English name |
|---|---|---|
| AVE | *Avena fatua* | Wild oat |
| ECH | *Echinochloa crusgalli* | Panic grass |
| LOL | *Lolium multiflorum* | Italian ryegrass |
| CYP | *Cyperus esculentus* | Chufa flat sedge |
| DIG | *Digitaria sanguinalis* | Hairy fingergrass |
| ALO | *Alopecurus myosuroides* | Slender foxtail |

| COMPOUND No. | HERBICIDAL ACTIVITY AT PRE-EMERGENCE Rate: 4 kg a.i./ha | | | | | |
|---|---|---|---|---|---|---|
|  | AVE | ECH | LOL | DIG | CYP | ALO |
| 3 | 5 | 5 | 5 | 5 | 5 | — |
| 4 | 3 | 5 | 4 | 5 | 5 | — |
| 6 | 5 | 5 | 5 | 5 | 5 | — |
| 8 | 0 | 4 | 2 | 5 | 0 | — |
| 14 | 5 | 5 | 5 | 5 | 3 | — |
| 17 | 5 | 5 | 5 | 5 | 5 | — |
| 22 | 5 | 4 | 5 | 3 | 0 | — |
| 23 | 5 | 5 | 5 | 3 | 1 | — |
| 27 | 3 | 5 | 5 | 5 | 4 | — |
| 28 | 5 | 4 | 5 | 4 | 3 | — |
| 29 | 5 | 5 | — | 5 | 4 | 5 |
| 37 | 4 | 5 | 5 | 5 | 0 | — |
| 40 | 3 | 5 | 5 | 5 | 3 | — |
| 41 | 1 | 4 | — | 5 | 1 | 5 |
| 42 | 5 | 5 | 5 | 5 | 4 | — |
| 44 | 5 | 5 | — | 5 | 4 | 5 |
| 46 | 0 | 3 | 4 | 4 | 0 | — |
| 47 | 5 | 5 | 5 | 5 | 1 | — |
| 52 | 5 | 5 | 5 | 5 | 5 | — |
| 53 | 5 | 5 | 5 | 5 | 4 | — |
| 54 | 5 | 5 | 5 | 5 | 5 | — |
| 56 | 5 | 5 | 5 | 5 | 4 | — |
| 59 | 5 | 5 | — | 5 | 5 | 5 |
| 60 | 2 | 5 | — | 5 | 3 | 4 |
| 61 | 5 | 5 | — | 5 | 4 | 5 |
| 62 | 5 | 5 | 5 | 5 | 3 | — |
| 63 | 4 | 4 | 3 | 3 | 0 | — |
| 65 | 5 | 5 | 5 | 5 | 5 | — |
| 66 | 3 | 5 | — | 5 | 3 | 5 |
| 67 | 4 | 5 | — | 5 | 3 | 5 |
| 69 | 5 | 5 | 5 | 5 | 4 | — |
| 70 | 5 | 5 | — | 5 | 4 | 5 |
| 72 | 5 | 5 | 5 | 5 | 5 | — |
| 73 | 4 | 3 | 5 | 4 | 5 | — |
| 81 | 5 | 5 | 5 | 5 | 5 | — |
| 82 | 5 | 5 | — | 5 | 5 | 5 |

HERBICIDAL ACTIVITY AT

-continued

| COMPOUND No. | POST-EMERGENCE Rate: 4 kg a.i./ha | | | | |
|---|---|---|---|---|---|
| | AVE | ECH | LOL | DIG | ALO |
| 3 | 0 | 4 | 3 | 4 | — |
| 6 | 2 | 3 | 2 | 4 | — |
| 17 | 4 | 3 | 3 | 1 | — |
| 23 | 3 | 3 | 2 | 0 | — |
| 27 | 0 | 2 | 3 | 3 | — |
| 28 | 3 | 4 | 4 | 2 | — |
| 40 | 1 | 4 | 3 | 3 | — |
| 42 | 0 | 4 | — | 3 | 4 |
| 44 | 3 | 4 | — | 4 | 4 |
| 52 | 1 | 3 | 4 | 3 | — |
| 53 | 0 | 4 | 2 | 3 | — |
| 54 | 1 | 3 | 3 | 1 | — |
| 56 | 0 | 4 | 3 | 3 | — |
| 59 | 0 | 4 | — | 4 | 3 |
| 60 | 0 | 4 | — | 2 | 4 |
| 63 | 0 | 4 | 2 | 3 | — |
| 65 | 0 | 3 | 3 | 3 | — |
| 72 | 4 | 3 | 4 | 2 | — |
| 81 | 0 | 4 | 4 | 3 | — |
| 82 | 0 | 4 | — | 2 | 4 |

EXAMPLE C

Selectivity Test in Major Crops with Herbicidal Application, at Pre-Emergence of the Plant Species A number of seeds, determined depending on the plant species and the size of the seed, are sown in 7×7×8 cm pots filled with light agricultural soil.

The seeds are then covered with a layer of soil approximately 3 mm in thickness.

The pots are then sprayed with a spraying mixture in a quantity corresponding to a volume application rate of 500 l/ha and containing the active ingredient at the required concentration.

The spraying mixture was prepared in the same way as in Example 41.

The treated pots are next placed in troughs intended to receive the moistening water, by sub-irrigation, and maintained at ambient temperature and 70% relative humidity for 24 days.

Scoring of the Herbicidal Activity

The reading is carried out in the following manner:

After 24 days, the destruction of the number of stalks in the treated pot is measured as a percentage (D) relative to the number of plants in the untreated (control) pots. The percentage reduction in size (SR) of the remaining treated plants is measured, relative to the control plants.

The percentage of foliage volume which is not destroyed by the product is therefore given by the formula $$([100-D] \times [100-SR])/100 = A$$

This value A is converted into a score of 0 to 5 according to the following scale:

| | | | Score | |
|---|---|---|---|---|
| 0 | A | 10 | 5 | (complete destruction) |
| 10 | A | 30 | 4 | |
| 30 | A | 50 | 3 | |
| 50 | A | 70 | 2 | |
| 70 | A | 90 | 1 | |
| 90 | A | 100 | 0 | (no effect) |

Thus, a product is judged to be selective towards the crop when the score value A is 0 or 1.

The results obtained are shown after Example C for application rates of 1 or 2 or 4 kg of active ingredient per hectare according to the products.

The plant species employed in this example are:

| Abbreviations | Latin name | English name |
|---|---|---|
| | 1) In the case of adventitious plants | |
| ECH | Echinochloa crus-galli | Panic grass |
| PAN | Panicum miliaceum | Common millet |
| DIG | Digitaria sanguinalis | Hairy fingergrass |
| SOR | Sorghum halepense | Johson grass |
| SET | Setaria faberii | Giant foxtail |
| | 2) In the case of the crops | |
| TRZ | Triticum aestivum | Spring wheat |
| ZEA | Zea mays | Maize |
| ORY | Oryza sativa | Rice |
| GLX | Glycine maximum | Soybean |

| | | SELECTIVITY TEST IN MAJOR CROPS HERBICIDAL ACTIVITY AT PRE-EMERGENCE | | | | | | | | | |
|---|---|---|---|---|---|---|---|---|---|---|---|
| Compound No. | Rate applied (kg/ha) | ECH | PAN | DIG | SOR | SET | CYP | TRZ | ZEA | ORY | GLX |
| 6 | 2 | 5 | 4 | 5 | 5 | 5 | 5 | 1 | 0 | 0 | 0 |
| 52 | 4 | 5 | 5 | 5 | 3 | 5 | 0 | 2 | 2 | 2 | 0 |
| 3 | 2 | 3 | 5 | 5 | 5 | 5 | 1 | 0 | 1 | 2 | 0 |
| 40 | 1 | 4 | 5 | 5 | 3 | 4 | 1 | 0 | 1 | 1 | 0 |
| 54 | 1 | 5 | 5 | 5 | 4 | 5 | 2 | 0 | 0 | 1 | 0 |
| 28 | 2 | 5 | 5 | 5 | 2 | 5 | 4 | 0 | 0 | 0 | 0 |
| 27 | 2 | 5 | 5 | 5 | 4 | 5 | — | 0 | 0 | 1 | 0 |
| 44 | 2 | 5 | 5 | 5 | 3 | 5 | — | 0 | 0 | 3 | 2 |

As can be seen in the table of results of this Example C, many products exhibit an excellent antigraminaceous activity at pre-emergence while exhibiting an excellent selectivity for 1 or 2 or 3 or 4 of the 4 crops tested=-spring wheat, maize, rice, soybean.

We claim:

1. A compound of formula:

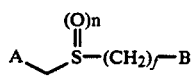

I in which:

n=2 f=0, 1

A is chosen from the groups in which:

Ar is chosen from the groups

Ar-1: phenyl with $(R_1)_m$

Ar-2: pyridyl with $(R_1)_p$

Ar-3: pyridyl with $(R_1)_p$

Ar-4: pyridyl with $(R_1)_p$

X being an oxygen or sulphur atom, $R_1$ being a halogen atom or a $C_1$–$C_4$ alkyl, $C_1$–$C_4$ alkoxy, $C_1$–$C_4$ haloalyl, $C_1$–$C_4$ haloalkoxy, nitro, cyano, $C_6$–$C_{10}$ aryl, $C_7$–$C_{11}$ aralkyl, $C_6$–$C_{10}$ aryloxy optionally substituted by 1 or 2 halogen atoms, or $C_7$–$C_{11}$ aralkyloxy group, optionally substituted by 1 or 2 halogen atoms, m=0, 1, 2, 3, 4, 5 p=0, 1, 2, 3, 4 the various radicals $R_1$ being identical or different when m or p is greater than or equal to 2

Y is a chlorine or bromine or iodine atom or an $OSO_2R_2$ group, $R_2$ being a $C_1$–$C_6$ alkyl, $C_6$–$C_{10}$ aryl or $C_7$–$C_{11}$ aralkyl group, the said groups being optionally substituted by 1 or 3 halogens or $C_1$–$C_4$ alkyl, $C_1$–$C_4$ alkoxy, $C_1$–$C_4$ haloalkyl, $C_1$–$C_4$ haloalkoxy or nitro groups, Z being a hydrogen atom or a (C=O)$R_{11}$ group, $R_{11}$ is hydrogen, $C_1$–$C_4$ alkyl, $C_1$–$C_4$ haloalkyl, B is chosen from the $C_1$–$C_{10}$ alkyl and $C_3$–$C_{10}$ cycloalkyl groups, these groups being optionally substituted by 1 to 6 halogen atoms or is chosen from the groups B1: phenyl with $(R_3)_k$ B2: pyridyl with $(R_3)_g$ and $(O)_{n'}$ B3: pyridyl with $(R_3)_g$ and $(O)_{n'}$ B4: pyridyl with $(R_3)_g$ and $(O)_{n'}$ $R_3$ having one of the meanings shown for $R_1$ or $NR_4R_5$, $S(O)_hR_6$ or (C=O)$R_7$, $R_4$ and $R_5$, which are identical or different, are hydrogen, $C_1$–$C_4$ alkyl or $C_6$–$C_{10}$ aryl, $R_6$ is $C_1$–$C_4$ alkyl, $R_7$ is $C_1$–$C_4$ alkyl, $C_1$–$C_4$ alkoxy, $C_1$–$C_4$ haloalkoxy or $NR_9R_{10}$, $R_9$ and $R_{10}$, which are identical or different, are hydrogen or $C_1$–$C_4$ alkyl, k=0, 1, 2, 3, 4, 5, g=0, 1, 2, 3, 4, h=0, 1, 2, n'=0, 1.

2. The compound according to claim 1, wherein X=0.

3. The compound according to claim 1, wherein m is smaller than or equal to 2.

4. The compound according to claim 1, wherein p is smaller than or equal to 2.

5. The compound according to claim 1, wherein k is smaller than or equal to 2.

6. The compound according to claim 1, wherein g is smaller than or equal to 1.

7. The compound according to claim 1, wherein $R_1$ is halogen, nitro, trifluoromethyl, methoxy or methyl.

8. The compound according to claim 1, wherein Z is hydrogen.

9. A herbicidal composition comprising 0.05 to 95% by weight of an active ingredient according to one of claims 1 or 2 to 8 in combination with the agriculturally acceptable solid or liquid carriers and the agriculturally acceptable surface-active agents.

10. A weeding process which consists in applying to the plants which are to be destroyed an effective quantity of a compound of formula (I) according to claim 1, at pre-emergence.

11. A compound according to claim 1 wherein $R_1$ is selected from the group consisting of Cl, Br, F, phenyl, naphthyl, benzyl, phenoxy, naphthoxy and benzyloxy.

12. The weeding process of claim 10 applied to plants selected from the group consisting of dicotyledon crops and maize crops.

13. A weeding process which consists of applying to the plants which are to be destroyed an effective quantity of a compound of formula (I) according to claim 1, at post emergence.

14. The weeding process of claim 10 applied to plants selected from the group consisting of dicotyledon crops and maize crops.

* * * * *

UNITED STATES PATENT AND TRADEMARK OFFICE
CERTIFICATE OF CORRECTION

Page 1 of 3

PATENT NO. : 5,100,460

DATED : March 31, 1992

INVENTOR(S) : Philippe Desbordes, et al.

It is certified that error appears in the above-identified patent and that said Letters Patent is hereby corrected as shown below:

Column 1, line 26: insert --Compounds of formula:--

Column 1, line 37: delete "Ar-1"

Column 1, line 42: delete "Ar-2"

Column 1, line 47: delete "Ar-3"

Column 1, line 53: delete "Ar-4"

Column 2, line 27: "$C_1-C_4$," should read as --$C_1-C_4$ alkyl,--

Column 3, line 25: delete "pO"

Column 7, line 13: "(A)" should read as --($A_1$)--

Column 7, line 44: "$_f$-" should read as --$_f$-B--

Column 7, line 62: after "at" insert --a--

Column 8, line 14: "(A)" should read as --($A_1$)--

Column 12, lines 45 & 46: "chloro-2," should read as --chloro-2'--

Column 12, line 49: "(3," should read as --(3'--

Column 13, line 38: "phenyl2" should read as --phenyl-2--

UNITED STATES PATENT AND TRADEMARK OFFICE
CERTIFICATE OF CORRECTION

PATENT NO. : 5,100,460

DATED : March 31, 1992

INVENTOR(S) : Philippe Desbordes, et al.

It is certified that error appears in the above-identified patent and that said Letters Patent is hereby corrected as shown below:

Column 13, lines 65 & 66: "[4," should read as --[4'--

Column 14, line 5: "50 d" should read as --50 cc--

Column 14, lines 27 & 29: "(2," should read as --(2'--

Column 14, line 38: "(2 ═" should read as --(2'--

Column 15, line 38: "1.6125" should read as --1,6125--

Column 17, line 20: "3--   [2'" should read as --3-[2'--

Column 18, line 38: "[3," should read as --[3'--

Column 18, line 46: "[3," should read as --[3'--

Column 20, line 41: "ar" should read as --are--

Column 22, line 63: "a" should read as --as--

Column 24, line 55: "o" should read as --on--

Column 25, line 48: "stage" should read as --stage.--

UNITED STATES PATENT AND TRADEMARK OFFICE
CERTIFICATE OF CORRECTION

PATENT NO. : 5,100,460
DATED : March 31, 1992
INVENTOR(S) : Philippe Desbordes, et al.

It is certified that error appears in the above-identified patent and that said Letters Patent is hereby corrected as shown below:

Column 28, line 27: "Johson" should read as --Johnson--

Column 29, line 38, Claim 1: "haloalyl" should read as --haloalkyl--

Signed and Sealed this

Seventh Day of September, 1993

Attest:

BRUCE LEHMAN

*Attesting Officer*     *Commissioner of Patents and Trademarks*